(12) United States Patent
Lange et al.

(10) Patent No.: US 9,757,165 B2
(45) Date of Patent: Sep. 12, 2017

(54) SPINAL IMPLANT SYSTEM AND METHOD

(71) Applicant: Warsaw Orthopedic, Inc., Warsaw, IN (US)

(72) Inventors: Eric C Lange, Collierville, TN (US); Darren L Davis, Arlington, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 14/921,332

(22) Filed: Oct. 23, 2015

(65) Prior Publication Data

US 2017/0112547 A1 Apr. 27, 2017

(51) Int. Cl.
*A61B 17/70* (2006.01)
*A61B 17/00* (2006.01)

(52) U.S. Cl.
CPC ... *A61B 17/7067* (2013.01); *A61B 2017/00862* (2013.01); *A61B 2017/7073* (2013.01)

(58) Field of Classification Search
CPC . A61B 17/7068; A61B 17/7076; A61B 17/70; A61B 17/7056; A61B 17/7067; A61B 17/7059; A61B 17/7071; A61B 50/30; A61B 50/33; A61B 50/20; A61B 2017/00862; A61B 2017/7073
USPC .......................................... 606/71, 246–279
See application file for complete search history.

(56) References Cited

U.S. PATENT DOCUMENTS

| | | | |
|---|---|---|---|
| 7,455,328 B2 | 11/2008 | Chelchowski et al. | |
| 8,308,768 B2 | 11/2012 | Fauth | |
| 8,343,190 B1 | 1/2013 | Muller et al. | |
| 8,603,143 B2 * | 12/2013 | Robinson | A61B 17/7068 606/249 |
| 8,882,805 B1 * | 11/2014 | Maccree | A61B 17/7067 606/249 |
| 8,906,064 B2 * | 12/2014 | Timm | A61B 17/7068 606/248 |
| 9,211,147 B2 * | 12/2015 | Gordon | A61B 17/7068 |
| 9,387,016 B2 * | 7/2016 | Okamoto | A61B 17/7065 |
| 2006/0241601 A1 * | 10/2006 | Trautwein | A61B 17/7049 606/248 |
| 2006/0247640 A1 | 11/2006 | Blackwell et al. | |
| 2007/0090238 A1 | 4/2007 | Justis | |
| 2007/0161994 A1 * | 7/2007 | Lowery | A61B 17/7032 606/86 A |
| 2008/0167688 A1 | 7/2008 | Fauth et al. | |
| 2010/0087869 A1 | 4/2010 | Abdou | |
| 2010/0148455 A1 | 6/2010 | Taguchi | |
| 2010/0268279 A1 | 10/2010 | Gabelberger et al. | |
| 2011/0004251 A1 | 1/2011 | Sweeney et al. | |
| 2011/0319936 A1 | 12/2011 | Gordon et al. | |

* cited by examiner

*Primary Examiner* — Pedro Philogene

(57) ABSTRACT

A spinal implant comprises a first member. A fastener is connected with the first member. A second member includes a deformable element engageable with the fastener such that the second member is translatable relative to the fastener in a first axial direction and translation of the second member relative to the fastener in a second axial direction is resisted and/or prevented. Systems and methods are disclosed.

20 Claims, 12 Drawing Sheets

SPINAL IMPLANT SYSTEM AND METHOD

TECHNICAL FIELD

The present disclosure generally relates to medical devices for the treatment of musculoskeletal disorders, and more particularly to a surgical system that includes a spinal implant and method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column.

Non-surgical treatments, such as medication, rehabilitation and exercise can be effective, however, may fail to relieve the symptoms associated with these disorders. Surgical treatment of these spinal disorders includes decompression, discectomy, laminectomy, laminoplasty, fusion, fixation and implantable prosthetics. For example, spinal stabilization treatments may employ implants, which may include interbody devices, plates and bone fasteners to stabilize vertebrae and facilitate healing. This disclosure describes an improvement over these technologies.

SUMMARY

In one embodiment, a spinal implant is provided. The spinal implant comprises a first member. A fastener is connected with the first member. A second member includes a deformable element engageable with the fastener such that the second member is translatable relative to the fastener in a first axial direction and translation of the second member relative to the fastener in a second axial direction is resisted and/or prevented. In some embodiments, systems and methods are provided.

BRIEF DESCRIPTION OF THE DRAWINGS

The present disclosure will become more readily apparent from the specific description accompanied by the following drawings, in which.

DETAILED DESCRIPTION

Figure 1:
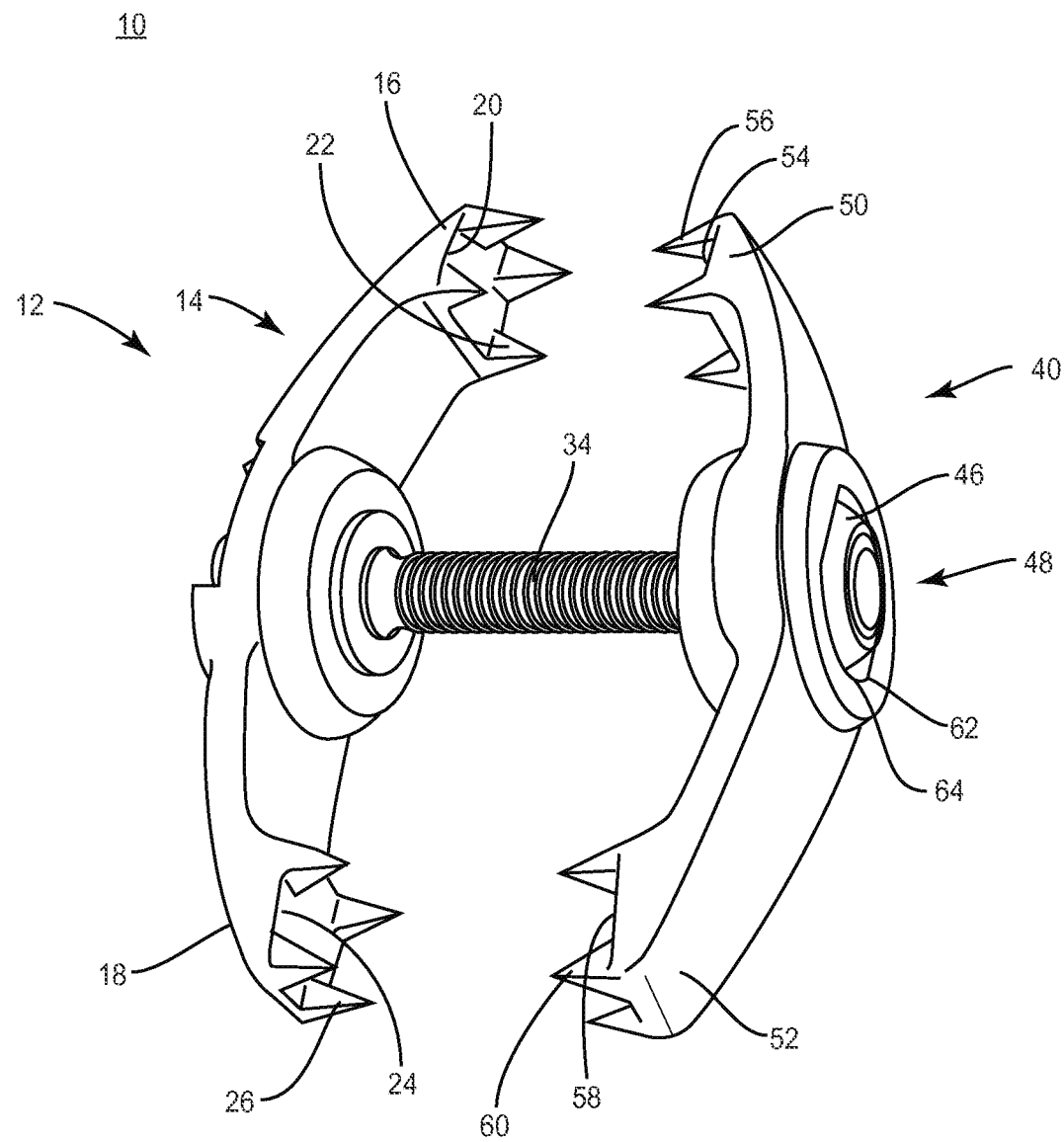
FIG. 1 is a perspective view of components of one embodiment of a surgical system in accordance with the principles of the present disclosure.
Figure 2:
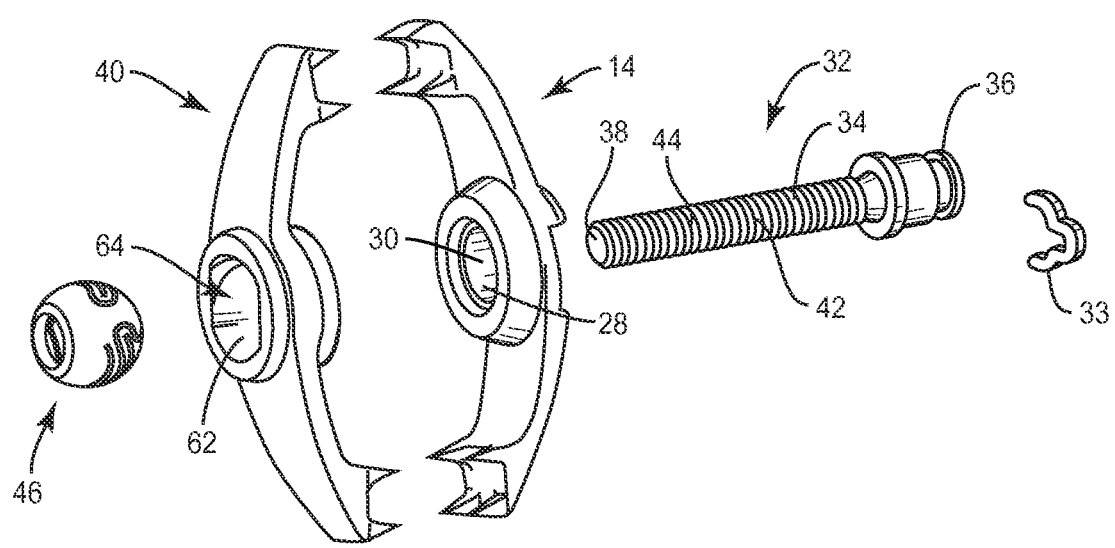
FIG. 2 is a perspective view of the components shown in FIG. 1 with parts separated.

The exemplary embodiments of the surgical system and related methods of use disclosed are discussed in terms of medical devices for the treatment of musculoskeletal disorders and more particularly, in terms of a surgical system including a spinal implant and a method for treating a spine.

In some embodiments, the surgical system includes a spinal implant that includes a spherical joint, which includes a spherical element. In some embodiments, the surgical system includes a spinal implant that includes a spherical joint, such as, for example, components of a ball and socket joint. In some embodiments, one or more components of the spherical joint can be a separate component and/or a subcomponent. In some embodiments, the components of the spherical joint facilitate rotation and/or translation of relative portions of the spinal implant. In some embodiments, the components of the spherical joint facilitate translation in one direction only of relative portions of the spinal implant.

In some embodiments, the spinal implant includes a spherical joint that provides single direction translation and/or rotation on a first side of the spinal implant. In some embodiments, a second side of the spinal implant includes a plate and a post, which are fixed to each other. In some embodiments, the spherical joint includes a spherical interface. In some embodiments, the spherical interface is configured for disposal with a movable plate.

In some embodiments, the spherical joint is configured to be ratcheted along a length of a post in one direction to resist and/or prevent back out. In some embodiments, the components of the spherical joint facilitate uni-directional relative movement of components of the spinal implant. In some embodiments, the spherical joint is configured to be unscrewed to back out components of the spinal implant from the post.

In some embodiments, the spherical joint is ratcheted down the post into a locking orientation. In some embodiments, the spherical interface is flexible and includes machined cavities, such as, for example, grooves that provide flexibility and allow for ratcheting of the spherical joint along the post. In some embodiments, the spherical joint is manufactured by machining cavities, such as, for example, internal threads and/or grooves within a sphere component of the spherical joint and a wire is used to machine the threads and/or grooves to create the flexibility. In some embodiments, the spinal implant includes a pedicle screw construct.

In some embodiments, the surgical system includes a spinal implant including a fastener utilized for securing together components of medical devices. In some embodiments, the fastener is designed to facilitate translation in a first direction along a threaded or ribbed post and prevent translation in a second, opposite direction. In some embodiments, the fastener is utilized in applications where two components, such as, for example, halves of a medical device are closed relative to each other to clamp tissue between the halves, such as, for example, a spinous process clamp. In some embodiments, the fastener has a spherical outer surface and is disposed inside a plate component that has a mating spherically shaped opening to facilitate multi-directional angulation.

In some embodiments, the fastener includes a channel and includes cavities, such as, for example, a series of serpentine cuts allowing portions of the fastener to compress in a spring-like manner. In some embodiments, when the fastener is compressed, the cuts can include threaded or ribbed portions along the inside of the fastener that allow a threaded or ribbed rod to move along relative to inner threaded or ribbed portions of the fastener. In some embodiments, the fastener is disposed with a plate and the spring-like portions of the fastener comprise a ratchet configuration to resist and/or prevent translation of the rod in an opposite direction. In some embodiments, the serpentine cuts are made directly into the plate component avoiding the need for a separate fastener piece. In some embodiments, the fastener includes at least one flat to prevent angulation of the plate relative to the fastener. In some embodiments, the fastener includes an outer threaded portion to facilitate a threaded engagement with the plate.

In some embodiments, the surgical system includes a spinal implant including a uni-directional fastener that allows for assembly and closure of implantable tissue clamping devices. In some embodiments, the fastener allows relative movement in one direction along a threaded post and relative multi-angular movement. In some embodiments, the fastener facilitates translation and rotation within one side of a spinous process plating implant. In some embodiments, the fastener can be adapted for a multitude of applications including attachment of rods to pre-positioned pedicle screws.

In some embodiments, the surgical system includes a spinal implant including a fastener that facilitates surgical implantation of a plurality of spinal implants. In some embodiments, the fastener reduces the number of steps within a surgical procedure for implantation with a multitude of surgical procedures.

In some embodiments, the surgical system includes a spinal implant including a spherical snap nut. In some embodiments, the nut includes one or more serpentine cuts to facilitate deflection of a portion of the nut as a tooth of a post is translated through the nut. In some embodiments, the nut includes an inner surface including teeth to engage a threaded post. In some embodiments, a post is translated through the nut in a first direction. In some embodiments, the nut includes a post engagement portion that is configured to flex in a first direction and resists and/or prevents the post from translating in a second direction.

In some embodiments, the surgical system includes a spinal implant including a spherical snap nut, a threaded post, a fixed plate and a movable plate. In some embodiments, the nut is configured for disposal in an opening of the movable plate by rotating the nut 90 degrees. In some embodiments, a portion of the opening includes a flange configured to retain the nut within the opening. In some embodiments, the fixed plate is not configured to rotate and/or translate relative to the threaded post. In some embodiments, the movable plate is configured for rotation and/or translation relative to the threaded post. In some embodiments, the movable plate translates in a first direction. In some embodiments, the threaded post moves in a second direction. In some embodiments, a portion of the plate prevents the nut from translating in a second direction opposite to the first direction to resist and/or prevent the threaded post from moving in that direction. In some embodiments, a threaded portion of the nut is flexible to allow the post to translate.

In some embodiments, the surgical system includes a spinal implant including a spinous process plate. In some embodiments, the spinous process plate includes an integrated spherical snap nut. In some embodiments, one or more serpentine cuts are incorporated directly into the spinous process plate. In some embodiments, the plate includes a ring configured to prevent a spring from translating in one direction thereby only allowing the threaded post to pass through in one direction. In some embodiments, the surgical system includes a pedicle screw including a spherical snap nut.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-5, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein. In one embodiment, a spinal implant, as described herein, may be formed substantially of a biocompatible metal, such as titanium and selectively coated with a bone-growth promoting material, such as HA. In one embodiment, a spinal implant, as described herein, may be formed substantially of a biocompatible polymer, such as PEEK, and selectively coated with a biocompatible metal, such as titanium, or a bone-growth promoting material, such as HA. In some embodiments, titanium may be plasma sprayed onto surfaces of the spinal implant to modify a radiographic signature of the spinal implant and/or improve bony ongrowth to the spinal implant by application of a porous or semi-porous coating of titanium.

Spinal implant system 10 may be employed, for example, with minimally invasive procedures, including percutaneous techniques, mini-open surgical techniques and/or open surgical techniques to deliver and introduce instrumentation and/or spinal implants, such as, for example, an interspinous implant at a surgical site within a body of a patient, which includes, for example, vertebrae. One or more of the components of spinal implant system 10 including an interspinous implant can be employed, for example, in decompression, discectomy, laminectomy, laminoplasty, fusion, fixation and implantable prosthetic procedures to treat patients suffering from a spinal disorder to provide stabilization and decompression. In some embodiments, one or more of the components of spinal implant system 10 is employed with a method for implanting an interspinous process spacer between two adjacent vertebrae, which includes introducing the interspinous spacer adjacent a superior spinous process and an inferior spinous process.

Spinal implant system 10 includes a spinal implant 12. In some embodiments, spinal implant 12 is configured to facilitate selective adjustability with a patient anatomy. Spinal implant 12 includes a member, such as, for example, an interspinous plate 14. Plate 14 extends between an end 16 and an end 18. In some embodiments, plate 14 is curved between end 16 and an end 18. In some embodiments, plate 14 includes a convexly curved side to provide an anatomical fit between the spinous processes and a concavely curved side to minimize posterior protrusion of plate 14 in the region between the spinous processes. In some embodiments, plate 14 may have alternate configurations, such as, for example, undulating, irregular, uniform, non-uniform, variable and/or tapered.

Plate 14 includes a surface 20 disposed at end 16. Surface 20 is configured to engage tissue, such as, for example, vertebrae, as described herein. In some embodiments, surface 20 includes teeth 22 configured to facilitate engagement with tissue. In some embodiments, surface 20 may be rough, textured, porous, semi-porous, dimpled, knurled, grooved and/or polished to facilitate engagement with tissue.

Plate 14 includes a surface 24 disposed at end 18. Surface 24 is configured to engage tissue, such as, for example, vertebrae, as described herein. In some embodiments, surface 24 includes teeth 26 configured to facilitate engagement with tissue. In some embodiments, surface 24 may be rough, textured, porous, semi-porous, dimpled, knurled, grooved and/or polished to facilitate engagement with tissue.

Plate 14 includes a surface 28 that defines an opening 30. Opening 30 is configured for disposal of a fastener, such as, for example, a post 32, as described herein. In some embodiments, plate 14 is fixedly connected with post 32 via a connector, such as, for example, a clip 33. Clip 33 is configured to fix post 32 with plate 14. In some embodiments, opening 30 is disposed intermediate or at a midpoint between end 16 and end 18. In some embodiments, opening 30 is disposed offset or staggered relative to end 16 and/or end 18.

Post 32 includes a shaft 34 that extends between an end 36 and an end 38. End 36 is configured for disposal with opening 30, as described herein. End 38 is configured for disposal with a member, such as, for example, an interspinous plate 40, as described herein. Shaft 34 has a cylindrical cross section. Shaft 34 includes an outer surface 42 having an external thread form 44 configured for engagement with a deformable element, such as, for example, a spheroidal nut 46, as described herein. In some embodiments, thread form 44 may include a single thread turn or a plurality of discrete threads. In some embodiments, other engaging structures may be located on shaft 34, such as, for example, a nail configuration, barbs, expanding elements, raised elements and/or spikes. In some embodiments, shaft 34 may have alternate configurations, such as, for example, arcuate, irregular, uniform, non-uniform, variable and/or tapered.

Plate 40 extends between an end 50 and an end 52. In some embodiments, plate 40 is curved between end 50 and an end 52. In some embodiments, plate 40 includes a convexly curved side to provide an anatomical fit between the spinous processes and a concavely curved side to minimize posterior protrusion of plate 40 in the region between the spinous processes. In some embodiments, plate 40 may have alternate configurations, such as, for example, undulating, irregular, uniform, non-uniform, variable and/or tapered.

Plate 40 includes a surface 54 disposed at end 50. Surface 54 is configured to engage tissue, such as, for example, vertebrae, as described herein. In some embodiments, surface 54 includes teeth 56 configured to facilitate engagement with tissue. In some embodiments, surface 54 may be rough, textured, porous, semi-porous, dimpled, knurled, grooved and/or polished to facilitate engagement with tissue.

Plate 40 includes a surface 58 disposed at end 52. Surface 58 is configured to engage tissue, such as, for example, vertebrae, as described herein. In some embodiments, surface 58 includes teeth 60 configured to facilitate engagement with tissue. In some embodiments, surface 58 may be rough, textured, porous, semi-porous, dimpled, knurled, grooved and/or polished to facilitate engagement with tissue. Plate 40 includes a surface 62 that defines a cavity 64 configured for disposal of spheroidal nut 46, as described herein.

Figure 6:
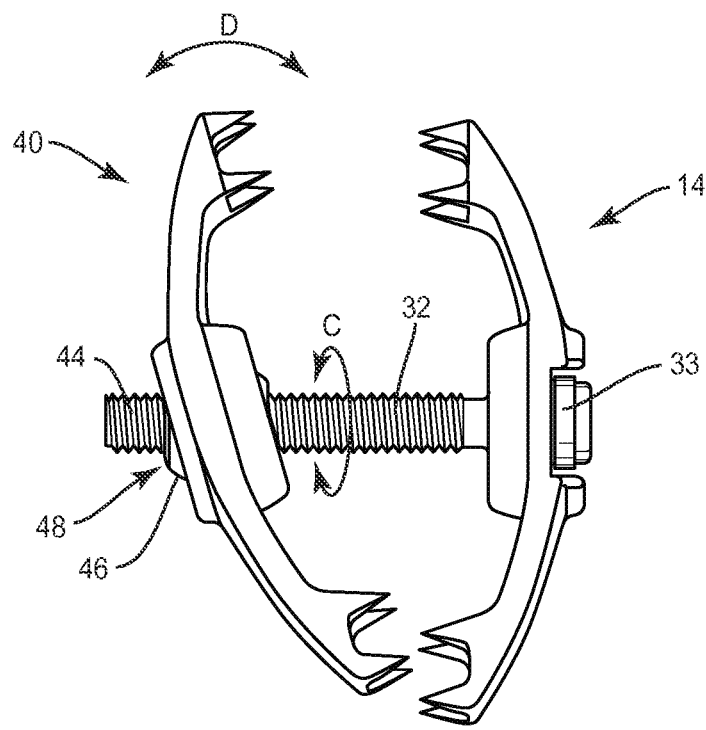
FIG. 6 is a side view of components of one embodiment of a surgical system in accordance with the principles of the present disclosure.

Plate 40 includes a spheroidal joint 48 that comprises cavity 64, spheroidal nut 46 and a portion of post 32 disposed within spheroidal nut 46. Spheroidal joint 48 is configured to facilitate axial translation of plate 40 and/or spheroidal nut 46 relative to post 32 and/or plate 14. In some embodiments, spheroidal joint 48 facilitates axial translation of plate 40 and/or spheroidal nut 46 relative to post 32 and/or plate 14 in a first axial direction, as shown by arrow A in FIG. 7, and to resist and/or prevent axial translation of plate 40 relative to post 32 in a second axial direction, opposite to the first direction, as shown by arrow B in FIG. 7. In some embodiments, spheroidal joint 48 comprises a ratchet such that plate 40 and/or spheroidal nut 46 are limited to axial translation in one direction only relative to post 32 and/or plate 14. In some embodiments, spheroidal joint 48 facilitates rotation of plate 40, including circumferentially about, as shown by arrows C in FIG. 6 and/or pivoting motion, as shown by arrows D in FIG. 6 in an axial plane, relative to spheroidal nut 46, post 32 and/or plate 14 in one or more directions. In some embodiments, spheroidal joint 48 facilitates multi-axial rotation of plate 40, as shown in FIG. 6, in one or a plurality of planes and/or to one or a plurality of axes relative to a longitudinal axis defined by post 32.

Surface 62 defines an opening communicating with cavity 64 that includes retaining elements, such as, for example, flanges 66. Flanges 66 are configured to extend inwardly with the opening of cavity 64 and retain spheroidal nut 46 with cavity as well as prevent spheroidal nut 46 from being expelled, driven and/or removed from cavity 64. Flanges 66 include linear surfaces on opposite sides of cavity 64 to facilitate insertion of a correspondingly shaped geometry of spheroidal nut 46, as described herein.

Figure 5:
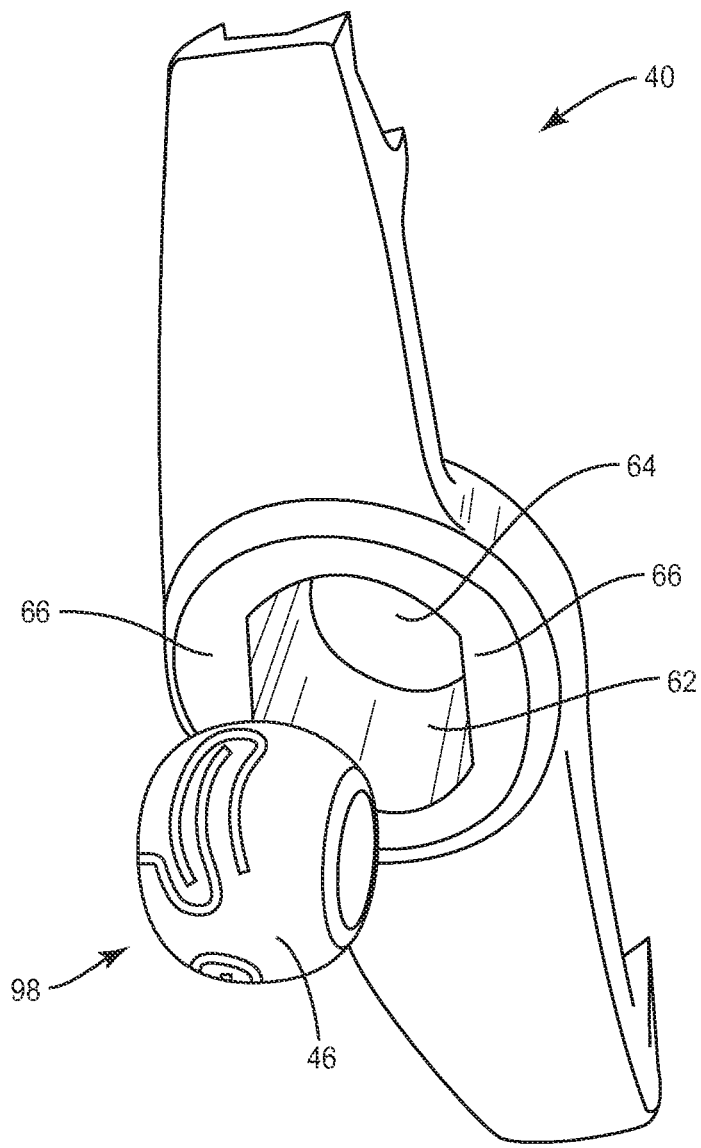
FIG. 5 is a side view of components of the system shown in FIG. 1.

In some embodiments, flat or planar configured ends 72, 74, as described herein, of spheroidal nut 46 are rotated into alignment with flanges 66, as shown in FIG. 5, for assembly of spheroidal nut 46 with plate 40. Spheroidal nut 46 is passed through the opening of cavity 64 as facilitated by flanges 66 and disposed with cavity 64. Within cavity 64, spheroidal nut 46 is rotated therein such that the outer surface of spheroidal nut 46 is oriented so that flanges 66 retain spheroidal nut 46 within cavity 64. In some embodiments, ends 72, 74 are aligned and disposed in a flat or planar configuration and configured for alignment with flanges 66 during assembly of the component parts of spinal implant 12 to facilitate assembly of spheroidal nut 46 with spheroidal joint 48 and plate 40. In some embodiments, surface 62 may include one or a plurality of flanges.

Figure 3:
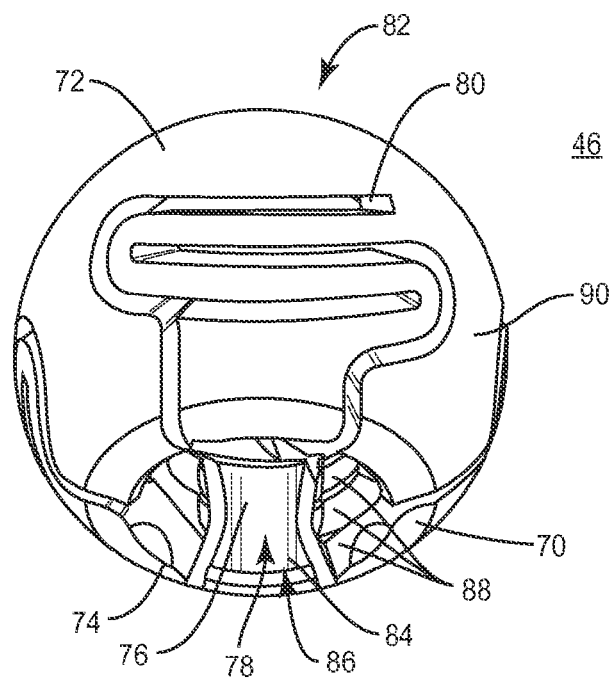
FIG. 3 is a perspective view of components of one embodiment of a surgical system in accordance with the principles of the present disclosure.
Figure 4:
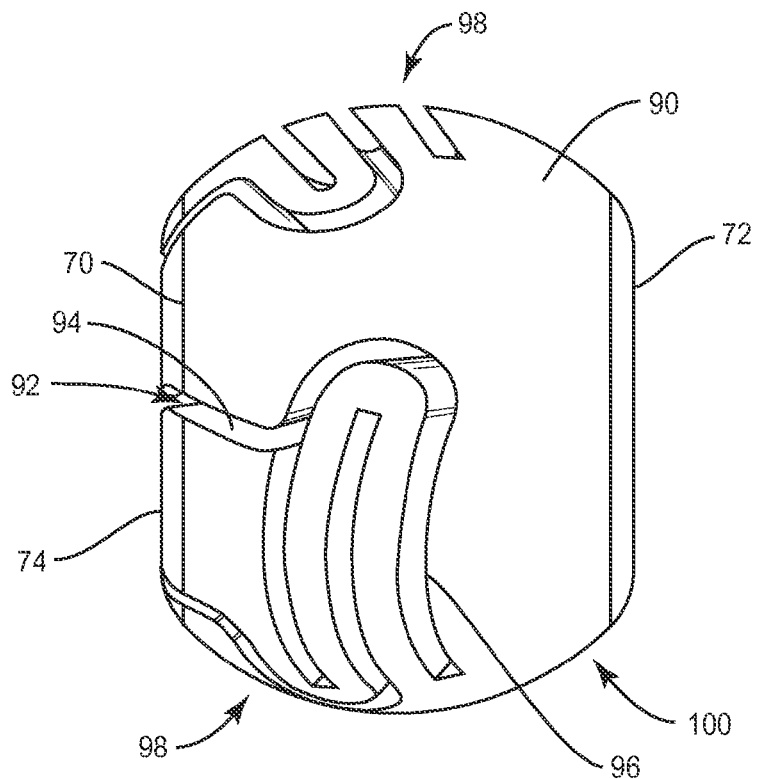
FIG. 4 is a side view of the components shown in FIG. 3.

Spheroidal nut 46 comprises a deformable element, such as, for example, a wall 70 that includes an inner surface 84 and an outer surface 90, as shown in FIGS. 3 and 4. Surface 84 defines an inner passageway 86 disposed along the body and axis of spheroidal nut 46. Passageway 86 extends between ends 72, 74 and defines openings 78, 82. Passageway 86 is configured for disposal and relative axial translation of post 32 therethrough. End 72 includes a surface 76 that defines opening 78. End 74 includes a surface 80 that defines opening 82.

Wall 70 includes a surface, such as, for example, a deformable wall portion 98 and a wall portion 100. Wall portion 98 is elastically deformable and/or resiliently biased to an expanded configuration of spheroidal nut 46. Wall portion 98 defines at least one cavity, such as, for example, a plurality of continuous pathways 92 to provide flexibility and elastic deformation of wall 70 in response to engagement with post 32, as described herein, and engagement of surfaces 62, 90 to overcome the resilient bias of wall portion 98 and dispose spheroidal nut 46 in a compressed or contracted configuration. In some embodiments, wall portion 98 can include one or a plurality of pathways. In some embodiments, all or only a portion of wall portion 98 includes an elastic configuration, relative to other components of spheroidal joint 48 and/or have elastic properties, such as the elastic properties corresponding to the material examples described above. In some embodiments, all or only a portion of wall portion 100 can be fabricated from a semi-rigid, rigid or elastic configuration, relative to other components of spheroidal joint 48 and corresponding to the material examples described above. In some embodiments, wall portion 98 is deformable relative to wall portion 100.

Pathways 92 are spaced apart and circumferentially disposed about surface 90. Pathways 92 are formed and extend between surfaces 84, 90. Wall portion 98 includes a plurality of linear portions 94 and a plurality of arcuate portions 96 such that each of pathways 92 define a sinuous configuration. In some embodiments, pathways 92 and/or spheroidal nut 46 are manufactured by machining cavities, such as, for example, internal threads and/or grooves within wall 70 and a wire is used to machine the threads and/or grooves to create flexibility of wall portion 98. In some embodiments, pathways 92 and/or spheroidal nut 46 are manufactured by machining cavities, such as, for example, a series of serpentine cuts allowing portions of spheroidal nut 46 and/or post 32 to compress in a spring-like manner. In some embodiments, pathways 92 and/or spheroidal nut 46 are manufactured by a water jet cutter using high pressure water to form cavities, such as, for example, a series of serpentine cuts allowing portions of spheroidal nut 46 and/or post 32 to compress in a spring-like manner.

Surface 84 includes at least one engagement element, such as, for example, teeth 88 configured for engagement with thread form 44 of post 32. Teeth 88 are formed with portions 94, 96 and extend inwardly to engage threads 44. In some embodiments, teeth 88 are disposed at an angular orientation. In some embodiments, one or more teeth 88 may have various configurations, for example, parallel, converging, diverging, irregular, tapered, offset, staggered, uniform and non-uniform. In some embodiments, surfaces 62, 90 engage, and threads 44 engage and slide over teeth 88, due to the angled orientation of threads 44 and resiliently biased configuration of teeth 88, in a first axial direction of translation of post 32 such that wall portion 98 elastically deforms in a spring like manner to compress or contract in the first direction. In some embodiments, threads 44 engage teeth 88 in an interference engagement such that wall portion 98 expands to its resiliently biased configuration and teeth 88 resist and/or prevent axial translation of post 32 in a second, opposite direction. In some embodiments, spheroidal joint 48 comprises a ratchet configuration including teeth 88 comprising a pawl and post 32 comprising a rack to resist and/or prevent translation of post 32 in the second direction, thereby limiting translation of post 32, as described herein, to only one direction.

Figure 7:
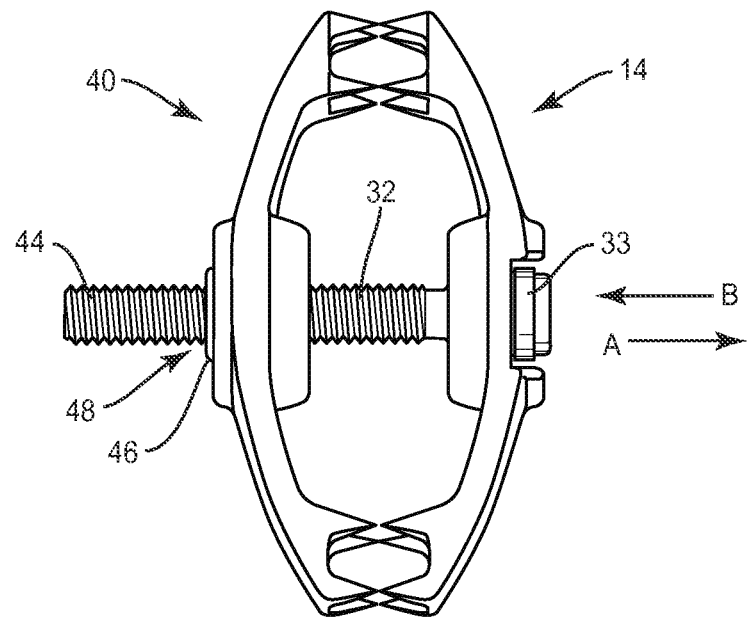
FIG. 7 is a side view of the components shown in FIG. 6.

In operation, for example, plate 40 and/or spheroidal nut 46 are selectively axially translated in an axial direction relative to post 32, which is fixed with plate 14, as shown in FIGS. 6 and 7. Post 32 axially translates, in the direction shown by arrow B in FIG. 8, such that surfaces 62, 90 engage and threads 44 engage and slide over teeth 88, due to the angled orientation of threads 44 and the elastically deformable configuration of teeth 88. Wall portion 98 elastically deforms in a spring like manner to compress or contract spheroidal nut 46 and facilitate axial translation of post 32 relative to spheroidal nut 46.

Figure 8:
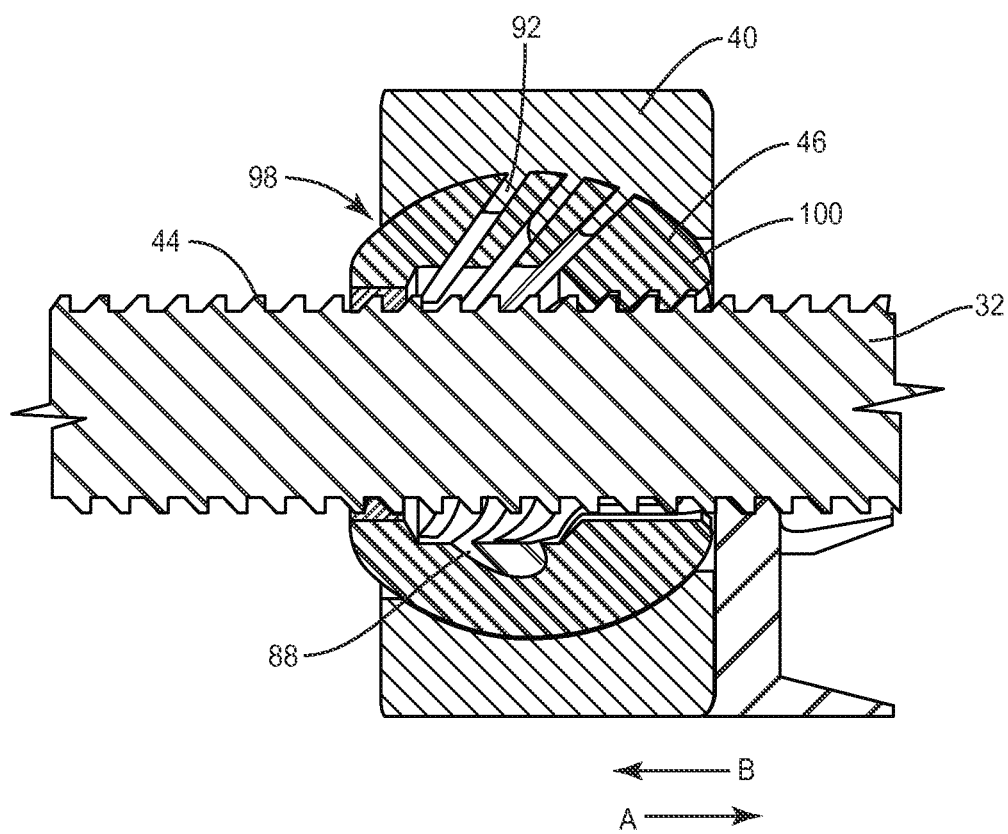
FIG. 8 is an enlarged cross section view of the components shown in FIG. 1.

Plate 40 is selectively rotated relative to spheroidal nut 46, post 32 and plate 14. Axial translation of post 32 in a second, opposite direction, as shown by arrow A in FIG. 8, is resisted and/or prevented such that threads 44 engage teeth 88 in an interference engagement. Wall portion 98 expands to its resiliently biased configuration and surface 90 engages surface 62 such that spheroidal joint 48 resists and/or prevents axial translation of plate 40 relative to post 32 in the axial direction shown by arrow B, and disengagement of spinal implant 12 from tissue. As such, in some embodiments, spheroidal joint 48 provides single direction translation and/or rotation on a selected side of spinal implant 12.

Figure 9:
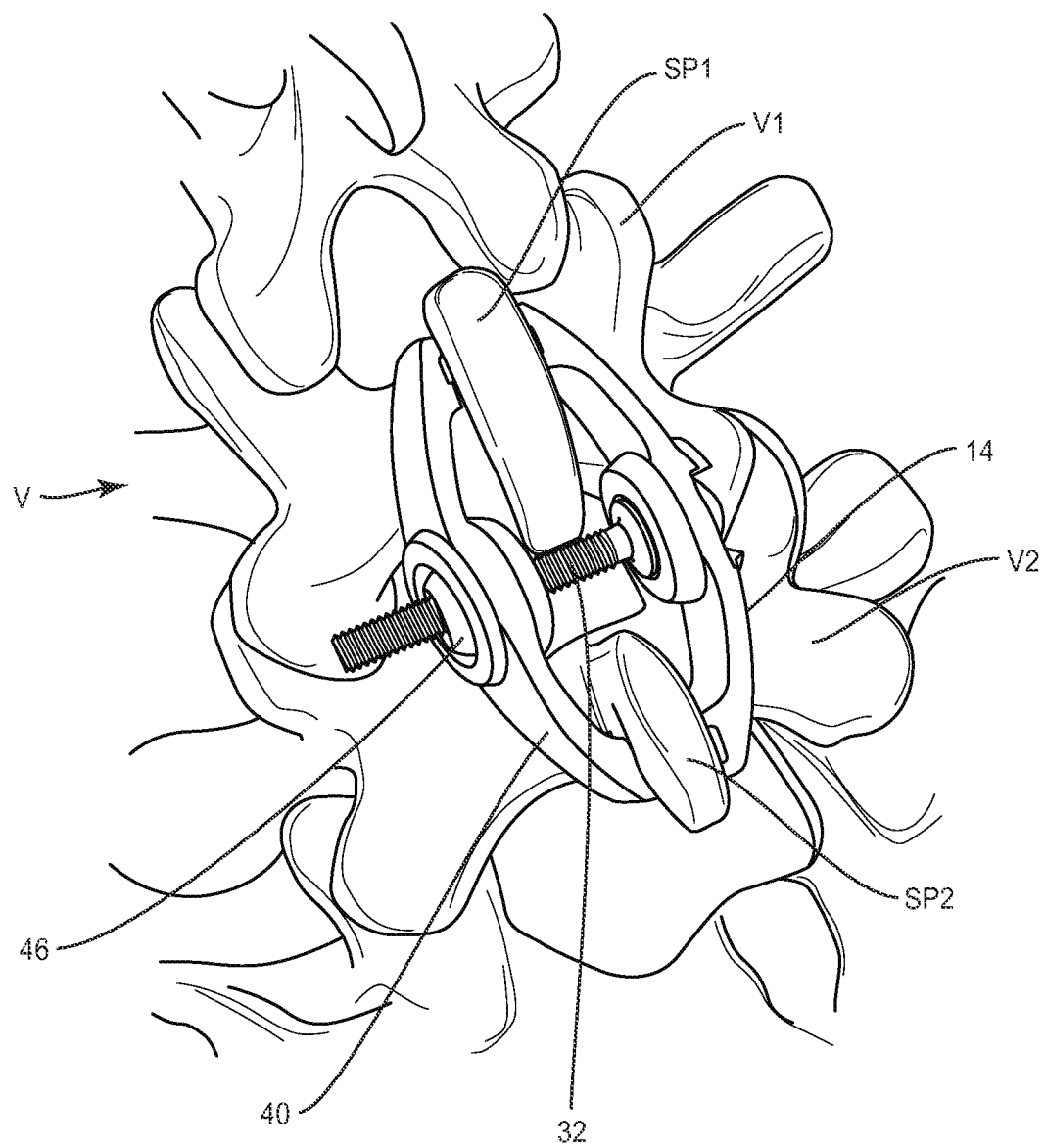
FIG. 9 is a perspective view of components of one embodiment of a surgical system in accordance with the principles of the present disclosure disposed with vertebrae.
Figure 10:
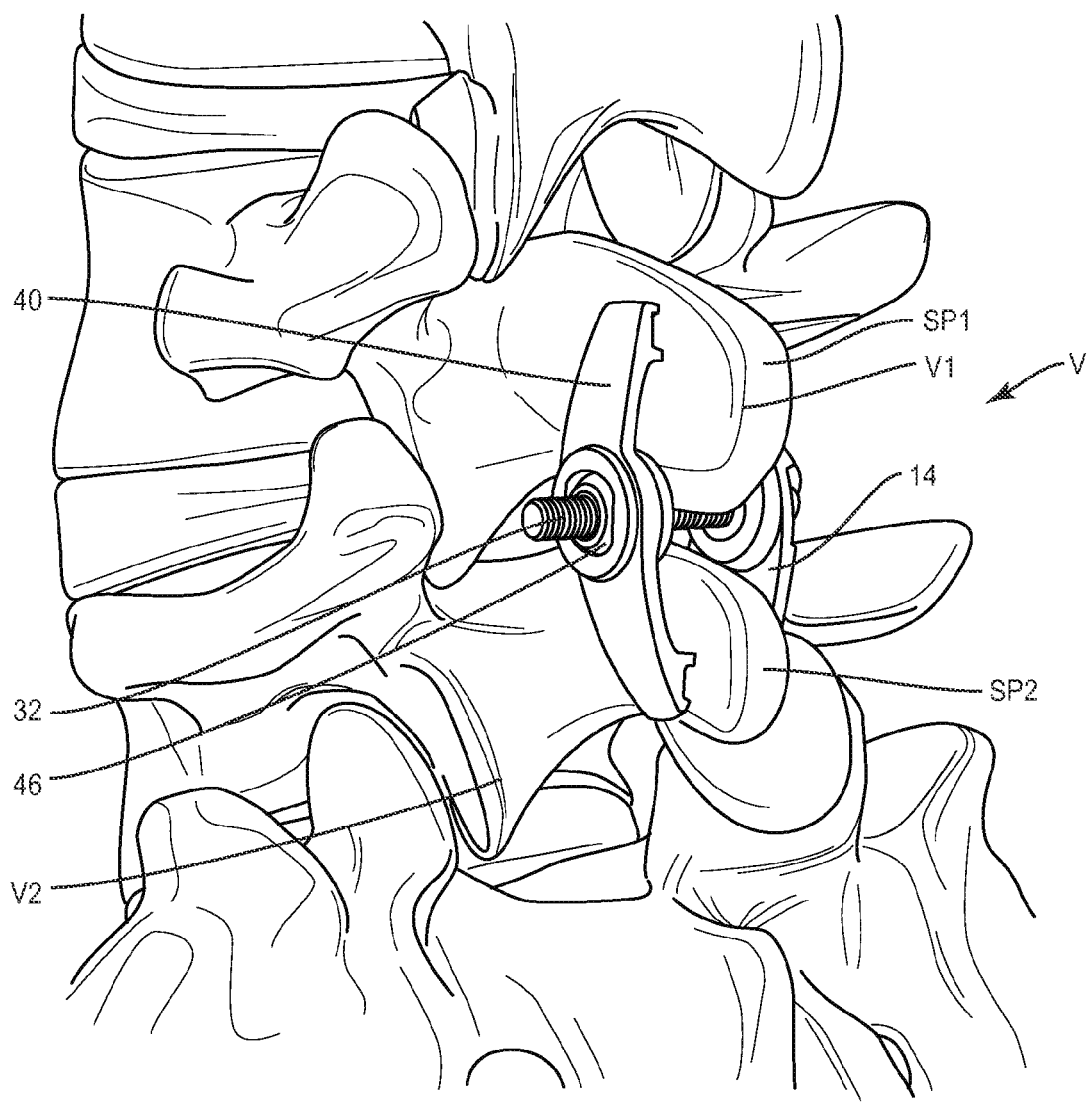
FIG. 10 is a perspective view of components of one embodiment of a surgical system in accordance with the principles of the present disclosure disposed with vertebrae.

In assembly, operation and use, spinal implant system 10, similar to the systems and methods described herein, is employed to treat a selected section of vertebrae V, as shown in FIGS. 9 and 10. A medical practitioner obtains access to a surgical site including vertebrae V in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating a spine disorder. In some embodiments, one or all of the components of spinal implant system 10 can be delivered or implanted as a pre-assembled device or can be assembled in situ. The components of spinal implant system 10 may be completely or partially revised, removed or replaced.

An incision is made in the body of a patient and a cutting instrument (not shown) creates a surgical pathway for implantation of components of spinal implant system 10 with a portion of vertebrae V including vertebra V1, vertebra V2, spinous process SP1 and spinous process SP2. A preparation instrument (not shown) can be employed to prepare tissue surfaces of vertebrae V, as well as for aspiration and irrigation of a surgical region.

Spinal implant 12, as described herein, is delivered and introduced to the surgical site adjacent spinous process SP1 and spinous process SP2. Plate 14 is fixed with post 32. Surface 20 is engaged with spinous process SP1 and surface 24 is engaged with spinous process SP2. Plate 40 is attached with post 32 such that spheroidal joint 48 is connected with post 32. Plate 40 and spheroidal nut 46 are selectively axially translated in an axial direction relative to post 32, which is fixed with plate 14, in the direction shown by arrow A in FIG. 7. Post 32 axially translates, in the direction shown by arrow B in FIG. 8, such that surfaces 62, 90 engage, and threads 44 engage and slide over teeth 88, as described herein. Wall portion 98 elastically deforms to compress or contract spheroidal nut 46.

Plate 40 is selectively rotated, as described herein, for alignment with spinous process SP1 and spinous process SP2. Surfaces 20, 54 engage spinous process SP1 and surfaces 24, 58 engage spinous process SP2 for implantation of spinal implant 12 with vertebrae V. Axial translation of post 32 in a second, opposite direction, as shown by arrow A in FIG. 8, is resisted and/or prevented such that threads 44 engage teeth 88 in an interference engagement. Wall portion 98 expands to its resiliently biased configuration and surface 90 engages surface 62 such that spheroidal joint 48 resists and/or prevents axial translation of plate 40 relative to post 32 in the axial direction shown by arrow B, and disengagement of spinal implant 12 from spinous process SP1 and spinous process SP2.

In some embodiments, spinal implant system 10 can include one or a plurality of plates and fasteners such as those described herein and/or fixation elements, which may be employed with a single vertebral level or a plurality of vertebral levels. In some embodiments, the plates and fasteners may be engaged with vertebrae in various orientations, such as, for example, series, parallel, offset, staggered and/or alternate vertebral levels. In some embodiments, the fasteners may be configured as multi-axial screws, sagittal angulation screws, pedicle screws, mono-axial screws, uniplanar screws, fixed screws, anchors, tissue penetrating screws, conventional screws, and/or expanding screws. In some embodiments, fasteners may be employed with wedges, anchors, buttons, clips, snaps, friction fittings, compressive fittings, expanding rivets, staples, nails, adhesives, posts, connectors, fixation plates and/or posts.

In some embodiments, spinal implant system 10 can include one or a plurality of spinal implants 12 provided in a set having various configurations and dimensions. In some embodiments, spinal implant 12 can be provided in various sizes from which a desired spacer member size and/or shape can be selected by a surgeon. In some embodiments, spinal implant system 10 can be provided in a kit or as a set, and spinal implant 12 provides a desired outer surface profile and size selected for placement between the spinous processes based on pre-operative planning or conditions encountered during surgery.

In some embodiments, spinal implant 12 can be made from a rigid material that positively prevents extension motion of the spinous processes. In some embodiments, spinal implant 12 is made from a compressible material to allow at least limited spinal extension motion between the spinous processes. In some embodiments, spinal implant 12 is made from an expandable material or is an expandable device that positively directs distraction forces between the spinous processes. In some embodiments, spinal implant 12 is compressible to initially fit between the spinous processes, and resiliently expands to positively exert a distraction force while yielding under compression forces to allow at least limited spinal extension motion.

In one embodiment, spinal implant system 10 includes an agent, which may be disposed, packed, coated or layered within, on, adjacent or about the components and/or surfaces of spinal implant system 10, and/or disposed with tissue. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiopaque markers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10.

Figure 11:
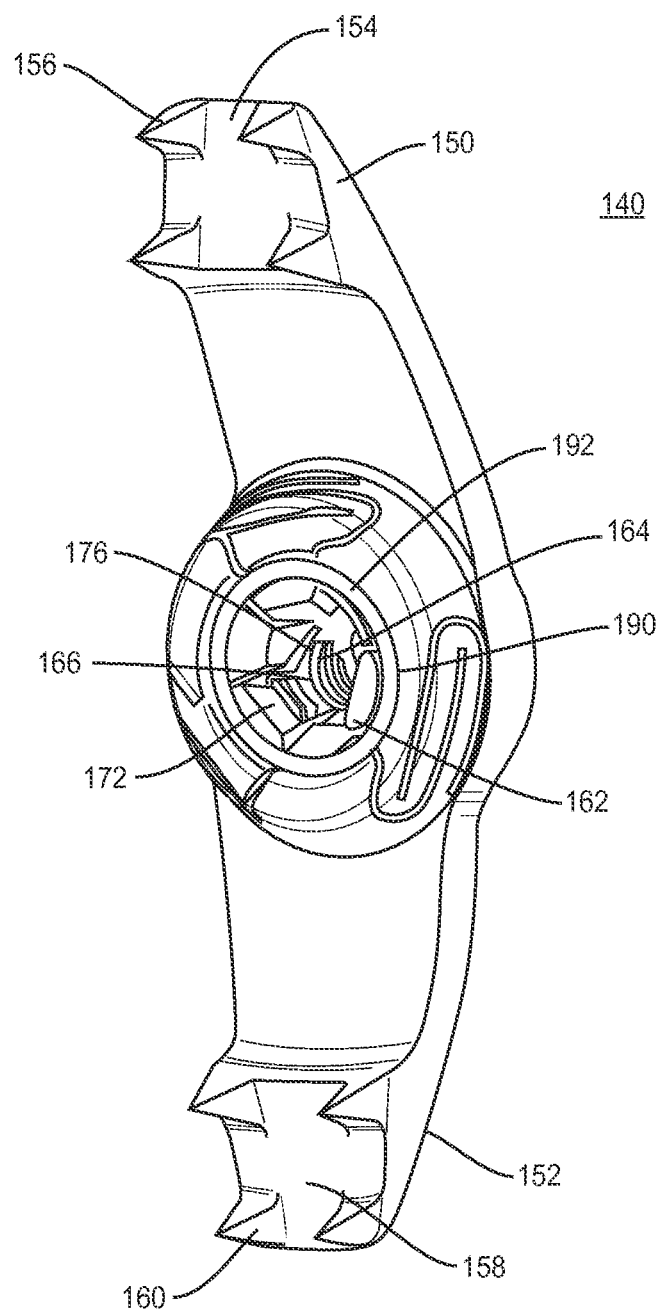
FIG. 11 is a perspective view of components of one embodiment of a surgical system in accordance with the principles of the present disclosure.
Figure 12:
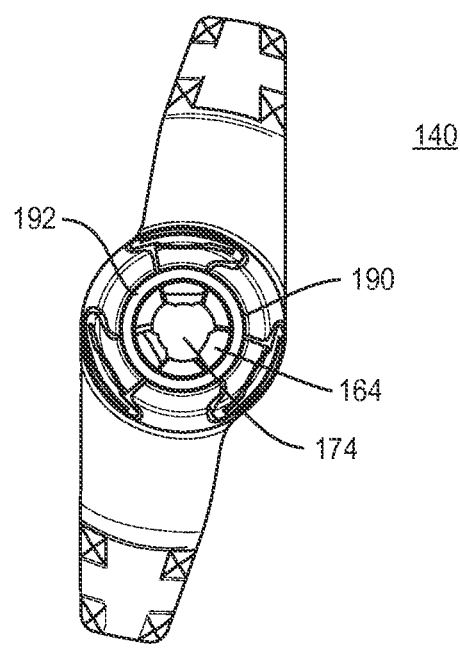
FIG. 12 is a side view of the components shown in FIG. 11.
Figure 13:
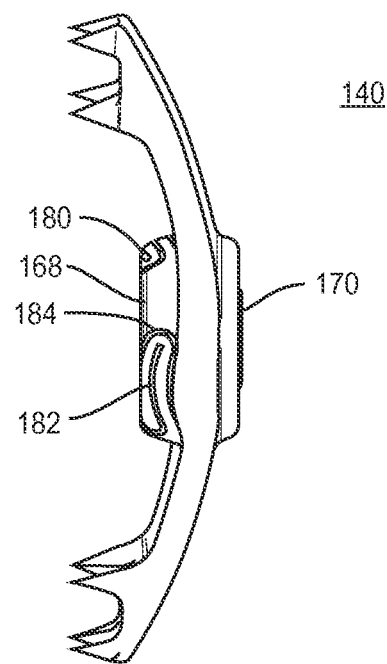
FIG. 13 is a side view of the components shown in FIG. 11.

In one embodiment, as shown in FIGS. 11-13, spinal implant system 10, similar to the systems and methods described herein, comprises spinal implant 12, described herein, which includes a plate 140, similar to plate 40 described herein, employed with plate 14 and post 32 described herein. Plate 140 extends between an end 150 and an end 152. Plate 140 includes a surface 154 disposed at end 150. Surface 154 is configured to engage tissue, such as, for example, vertebrae, as described herein. In some embodiments, surface 154 includes teeth 156 configured to facilitate engagement with tissue. Plate 140 includes a surface 158 disposed at end 152. Surface 158 is configured to engage tissue, such as, for example, vertebrae, as described herein. In some embodiments, surface 158 includes teeth 160 configured to facilitate engagement with tissue.

Plate 140 includes a surface 162 that defines a spheroidal joint 164, similar to spheroidal joint 48 described herein, which is integrally connected and/or monolithically formed with plate 140. Spheroidal joint 164 is configured to facilitate axial translation of plate 140 relative to post 32 and/or plate 14. In some embodiments, spheroidal joint 164 facilitates axial translation of plate 140 relative to post 32 and/or plate 14 in a first axial direction and to resist and/or prevent axial translation of plate 140 relative to post 32 in a second axial direction, opposite to the first direction, similar to that described herein. In some embodiments, spheroidal joint 164 comprises a ratchet such that plate 140 is limited to axial translation in one direction only relative to post 32 and/or plate 14. In some embodiments, spheroidal joint 164 facilitates rotation of plate 140, including circumferentially about and/or pivoting motion, in an axial plane, relative to post 32 and/or plate 14 in one or more directions. In some embodiments, spheroidal joint 164 facilitates multi-axial rotation of plate 140 in one or a plurality of planes and/or to one or a plurality of axes relative to a longitudinal axis defined by post 32.

Spheroidal joint 164 comprises a deformable element, such as, for example, a wall 166, similar to wall 70 described herein. Spheroidal joint 164 extends between an end 168 and an end 170. Spheroidal joint 164 includes a surface 172. Surface 172 defines a passageway 174 that extends between end 168 and end 170. Passageway 174 is configured for disposal of post 32.

Surface 172, similar to wall portion 98 described herein, is elastically deformable and/or resiliently biased to an expanded configuration of spheroidal joint 164. Surface 172 defines at least one cavity, such as, for example, a plurality of continuous pathways 180 to provide flexibility and elastic deformation of wall 166 in response to engagement with post 32, as described herein, to overcome the resilient bias of surface 172 and dispose spheroidal joint 164 in a compressed or contracted configuration. In some embodiments, surface 172 can include one or a plurality of pathways. In some embodiments, all or only a portion of surface 172 includes an elastic configuration, relative to other components of spheroidal joint 164 and/or have elastic properties, such as the elastic properties corresponding to the material examples described above.

Pathways 180 are spaced apart and circumferentially disposed about surface 172. Pathways 180 are formed and extend between ends 168, 170. Surface 172 includes a plurality of linear portions 182 and a plurality of arcuate portions 184 such that each of pathways 180 define a sinuous configuration. In some embodiments, pathways 180 are manufactured by machining cavities, such as, for example, internal threads and/or grooves within wall 166 and a wire is used to machine the threads and/or grooves to create flexibility of surface 172. In some embodiments, pathways 180 are manufactured by machining cavities, such as, for example, a series of serpentine cuts allowing portions of spheroidal joint 164 and/or post 32 to compress in a spring-like manner.

Surface 172 includes at least one engagement element, such as, for example, teeth 176, similar to teeth 88 described herein, are configured for engagement with thread form 44 of post 32. Teeth 176 are formed with portions 182, 184 and extend inwardly to engage threads 44. In some embodiments, threads 44 engage and slide over teeth 176, due to the angled orientation of threads 44 and resiliently biased configuration of teeth 176, in a first axial direction of translation of post 32 such that surface 172 elastically deforms in a spring like manner to compress or contract in the first direction. In some embodiments, threads 44 engage teeth 176 in an interference engagement such that surface 172 expands to its resiliently biased configuration and teeth 176 resist and/or prevent axial translation of post 32 in a second, opposite direction.

Surface 172 includes a groove 190. Groove 190 is disposed circumferentially about teeth 176. Groove 190 is configured for disposal of a ring 192. Ring 192 is configured to resist and/or prevent deformation of spheroidal joint 164 to resist and/or prevent translation of post 32 in a second, opposite direction, as described herein. In operation, plate 140 with spheroidal joint 164 are selectively axially translated in a direction relative to post 32, which is fixed with plate 14, similar to that described herein. Post 32 axially translates such that spheroidal joint 164 deforms, similar to that described herein, and threads 44 engage and slide over teeth 176 due to the elastically deformable configuration of teeth 176. Surface 172 elastically deforms in a spring like manner to facilitate axial translation of post 32 relative to spheroidal joint 164.

Plate 140 is selectively rotated relative to spheroidal joint 164, post 32 and plate 14, similar to that described herein. Axial translation of post 32 in a second, opposite direction is resisted and/or prevented such that threads 44 engage teeth 176 in an interference engagement. Ring 192 resists and/or prevents deformation of spheroidal joint 164 to resist and/or prevent translation of post 32 in a second, opposite direction, and disengagement of spinal implant 12 from tissue.

Figure 14:
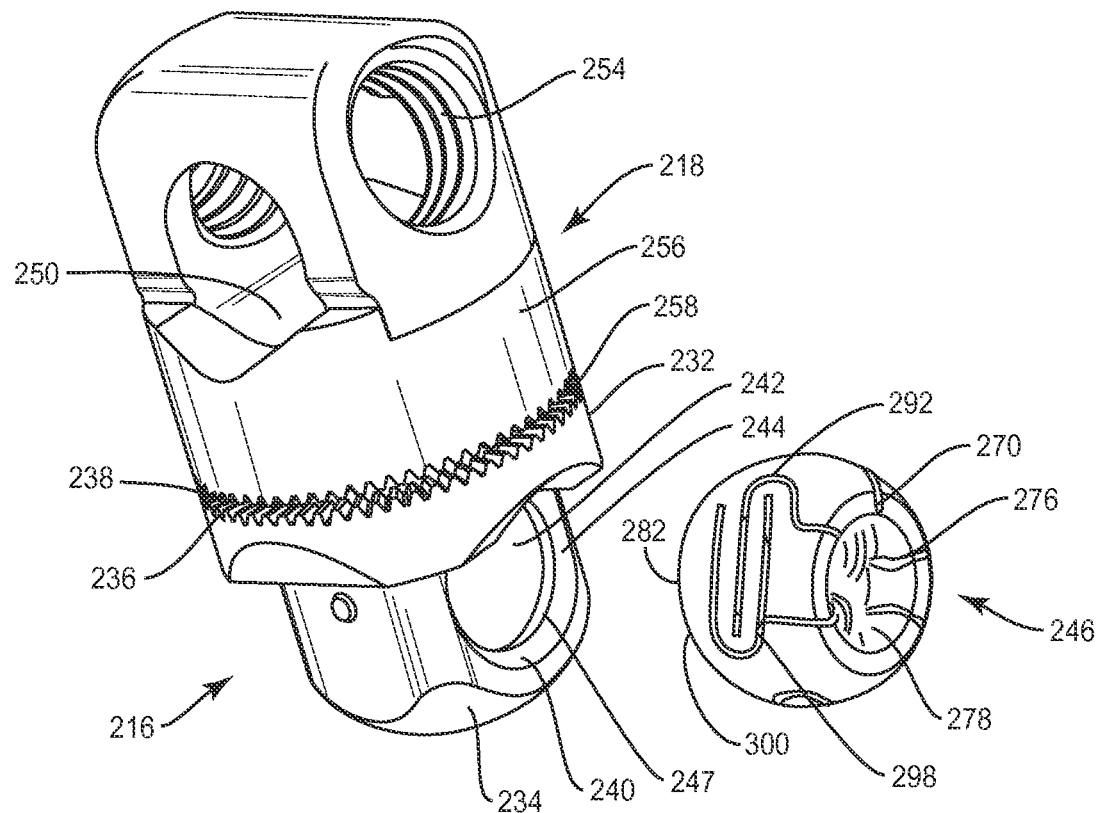
FIG. 14 is a perspective view of components of one embodiment of a surgical system in accordance with the principles of the present disclosure with parts separated.
Figure 15:
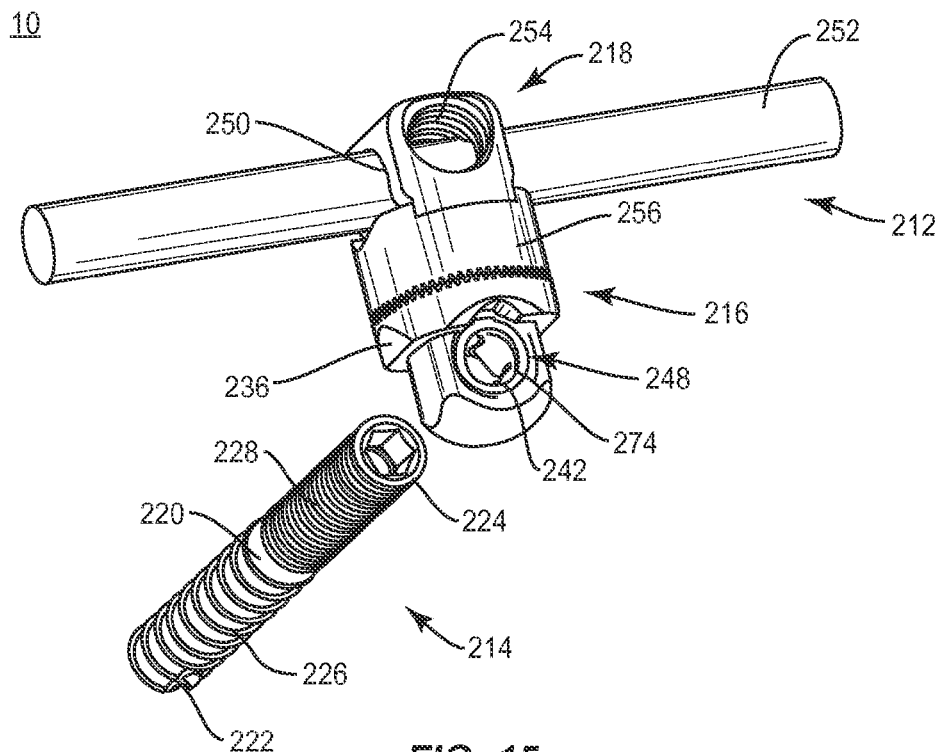
FIG. 15 is a perspective view of components of one embodiment of a surgical system in accordance with the principles of the present disclosure with parts separated.
Figure 16:
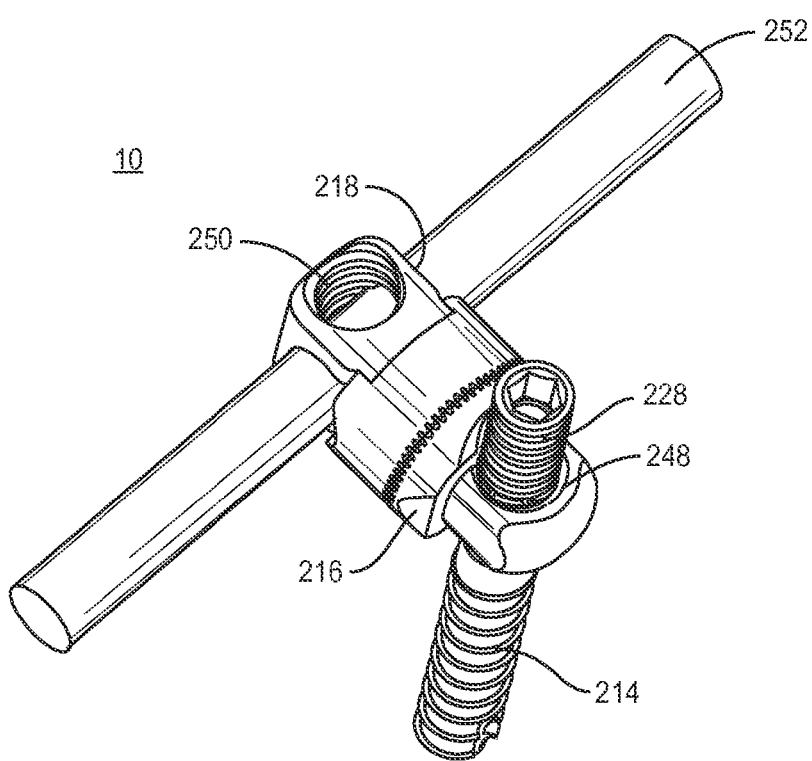
FIG. 16 is a perspective view of the components shown in FIG. 15.

In one embodiment, as shown in FIGS. 14-16, spinal implant system 10, similar to the systems and methods described herein, includes a spinal implant, such as, for example, a pedicle screw construct 212. Pedicle screw construct 212 includes a bone screw 214, a connector 216, a receiver 218, and a spheroidal nut 246, similar to spheroidal nut 46 described with regard to FIGS. 1-10.

Bone screw 214 includes a shaft 220 that extends between an end 222 and an end 224. End 222 is configured for fixation with tissue, such as, for example, vertebrae. End 224 is configured for disposal with connector 216, as described herein. Shaft 220 has a cylindrical cross section. Shaft 220 includes an outer surface 226 having an external thread form 228 configured for engagement with spheroidal nut 246. In some embodiments, the thread form may include a single thread turn or a plurality of discrete threads. In some embodiments, other engaging structures may be located on shaft 220, such as, for example, a nail configuration, barbs, expanding elements, raised elements and/or spikes. In some embodiments, shaft 220 may have alternate configurations, such as, for example, arcuate, irregular, uniform, non-uniform, variable and/or tapered.

Connector 216 extends between an end 232 and an end 234. End 232 includes a disk 236 having a splined surface 238. Splined surface 238 is configured to mate with splines on a surface of receiver 218 to releasably fix receiver 218 with connector 216 in a selected rotatable position, as described herein. In some embodiments, receiver 218 may be coupled with connector 216 in alternate fixation configurations, such as, for example, friction fit, pressure fit, locking protrusion/recess, locking keyway and/or adhesive. In some embodiments, receiver 218 may be disposed with connector 216 for relative movement thereto, such as, for example, transverse, perpendicular and/or other angular orientations, such as acute or obtuse, co-axial and/or may be offset or staggered. In some embodiments, receiver 218 may move relative to connector 216 in alternate planes relative to a body, such as, for example, transverse and/or sagittal planes of a body.

End 234 includes a surface 240 that defines a cavity 242. End 234 includes a spheroidal joint 248, similar to spheroidal joint 48 described herein, which comprises cavity 242, spheroidal nut 246 and a portion of bone screw 214 disposed within spheroidal nut 246. Spheroidal joint 248 is configured to facilitate axial translation of connector 216 and/or spheroidal nut 246 relative to bone screw 214 and/or tissue. In some embodiments, spheroidal joint 248 facilitates axial translation of connector 216 and/or spheroidal nut 246 relative to bone screw 214 and/or tissue in a first axial direction and resists and/or prevents axial translation of connector 216 relative to bone screw 214 in a second axial direction, similar to that described herein. In some embodiments, spheroidal joint 248 comprises a ratchet such that connector 216 and/or spheroidal nut 246 are limited to axial translation in one direction only relative to bone screw 214 and/or tissue. In some embodiments, spheroidal joint 248 facilitates rotation of connector 216, including circumferentially about and/or pivoting motion in an axial plane, relative to spheroidal nut 246, bone screw 214 and/or tissue in one or more directions. In some embodiments, spheroidal joint 248 facilitates multi-axial rotation of connector 216 in one or a plurality of planes and/or to one or a plurality of axes relative to a longitudinal axis defined by bone screw 214.

Cavity 242 includes a retaining element, such as, for example, a circumferential flange 244. Flange 244 is configured to extend into a portion of cavity 242 to prevent spheroidal nut 246 from being expelled, driven and/or translated from cavity 242.

Receiver 218 is attachable to end 232 of connector 216 and is selectively rotatable in a plane of the body and selectively fixable in a position within the plane. Receiver 218 includes a body portion having an implant cavity 250. Implant cavity 250 is configured to receive and movably support at least a portion of an implant, such as, for example, a vertebral rod 252, such that the implant can translate axially within implant cavity 250. Implant cavity 250 is rotatable such that vertebral rod 252 disposed in implant cavity 250 is rotatable in a first plane, such as, for example, a coronal plane of the body, relative to connector 216 in a configuration for selective fixation with connector 216. Receiver 218 includes a threaded cavity 254 configured to receive a coupling member, such as, for example, a setscrew to releasably fix vertebral rod 252 within implant cavity 250 in a selected position. In some embodiments, vertebral rod 252 is attachable with one or more vertebral levels via fasteners and/or spinal constructs, as described herein.

Receiver 218 includes a disk 256 having a face defining a splined surface 258 configured to mate with splined surface 238 of connector 216 in a selected rotatable position. Surfaces 238, 258 are configured to mesh such that receiver 218 can rotate and lock at different angles relative to connector 216.

Spheroidal nut 246 comprises a deformable element, such as, for example, a wall 270, similar to wall 70 described herein, which includes an inner surface defining an inner passageway and an outer surface. The inner passageway extends between openings 278, 282. The inner passageway is configured for disposal and relative axial translation of bone screw 214 therethrough.

Wall 270 includes a deformable wall portion 298, similar to wall portion 98 described herein, and a wall portion 300, similar to wall portion 100 described herein. Wall portion 298 is elastically deformable and/or resiliently biased to an expanded configuration of spheroidal nut 246. Wall portion 298 defines at least one cavity, such as, for example, a plurality of continuous pathways 292, similar to pathways 92 described herein, to provide flexibility and elastic deformation of wall 270 in response to engagement with bone screw 214, similar to that described herein, and engagement of surface 240 and the outer surface of spheroidal nut 246 to overcome the resilient bias of wall portion 298 and dispose spheroidal nut 246 in a compressed or contracted configuration.

Pathways 292 are spaced apart and circumferentially disposed about the outer surface of spheroidal nut 246. In some embodiments, wall portion 298 one or a plurality of cavities, as described herein. The inner surface of spheroidal nut 246 includes at least one engagement element, such as, for example, teeth 276, similar to teeth 88 described herein, being configured for engagement with thread form 228 of bone screw 214. In some embodiments, surface 240 and the outer surface of spheroidal nut 246 engage, and threads 228 engage and slide over teeth 276, due to the resiliently biased configuration of teeth 276, in a first axial direction of translation of bone screw 214 such that wall portion 298 elastically deforms in a spring like manner to compress or contract in the first direction. In some embodiments, threads 228 engage teeth 276 in an interference engagement such that wall portion 298 expands to its resiliently biased configuration and teeth 276 resist and/or prevent axial translation of bone screw 214 in a second, opposite direction. In some embodiments, spheroidal joint 248 comprises a ratchet configuration including teeth 276 comprising a pawl and bone screw 214 comprising a rack to resist and/or prevent translation of bone screw 214 in the second direction, thereby limiting translation of bone screw 214, as described herein, to only one direction.

In operation, for example, bone screw 214 and/or vertebral rod 252 are attached with vertebrae. Connector 216 and/or spheroidal nut 246 are selectively axially translated in an axial direction relative to bone screw 214, similar to that described herein. Bone screw 214 axially translates such that surface 240 and the outer surface of spheroidal nut 246 engage and threads 228 engage and slide over teeth 276 due to the elastically deformable configuration of teeth 276. Wall portion 298 elastically deforms in a spring like manner to compress or contract spheroidal nut 246 and facilitate axial translation of bone screw 214 relative to spheroidal nut 246.

Connector 216 is selectively rotated relative to spheroidal nut 246, bone screw 214 and tissue. Axial translation of bone screw 214 in a second, opposite direction is resisted and/or prevented such that threads 228 engage teeth 276 in an interference engagement. Wall portion 298 expands to its resiliently biased configuration and surface 240 engages the outer surface of spheroidal nut 246 such that spheroidal joint 248 resists and/or prevents axial translation of connector 216 relative to bone screw 214 in the axial direction.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
a first member comprising an opening;
a fastener comprising a head and a post that extends from the head, a portion of the head being positioned within the opening, the head having a maximum diameter that is greater than that of the opening; and
a second member including a deformable element engageable with the post such that the second member is translatable relative to the fastener in a first axial direction and translation of the second member relative to the fastener in a second axial direction is resisted and/or prevented.

2. A spinal implant as recited in claim 1, wherein the second member comprises a spheroidal joint including the deformable element.

3. A spinal implant as recited in claim 1, wherein the deformable element includes a surface defining at least one cavity.

4. A spinal implant as recited in claim 3, wherein the at least one cavity comprises a sinuous configuration.

5. A spinal implant as recited in claim 3, wherein the at least one cavity comprises a continuous pathway including a plurality of linear portions and arcuate portions.

6. A spinal implant as recited in claim 1, wherein the deformable element includes a wall defining a plurality of cuts.

7. A spinal implant as recited in claim 1, wherein the post comprises a threaded outer surface and the deformable element includes a wall including at least one tooth engageable with the threaded outer surface.

8. A spinal implant as recited in claim 1, wherein the post comprises a threaded outer surface and the deformable element includes a resiliently biased wall including at least one tooth engageable with the threaded outer surface.

9. A spinal implant as recited in claim 1, wherein the second member is rotatable relative to the fastener and/or the deformable element.

10. A spinal implant as recited in claim 1, wherein the second member defines a spherical cavity and the deformable element comprises a spherical nut disposed for rotation within the spherical cavity.

11. A spinal implant as recited in claim 10, wherein the second member includes at least one flange adjacent the spherical cavity.

12. A spinal implant as recited in claim 1, wherein the deformable element includes a barrel shaped cross section.

13. A spinal implant as recited in claim 1, wherein the deformable element is elastically deformable in the first direction only.

14. A spinal implant as recited in claim 1, wherein the deformable element is monolithically formed with the second member.

15. A spinal implant as recited in claim 1, wherein the first member is fixed relative to the fastener.

16. A spinal implant comprising:
a first member comprising an opening;
a fastener comprising a head and a post that extends from the head, a portion of the head being positioned within the opening, the head having a maximum diameter that is greater than that of the opening; and
a second member translatable relative to the fastener in a first axial direction and including a spherical nut having a wall engageable with the post, the wall being deformable in the first direction only such that translation of the second member relative to the fastener in a second axial direction is resisted and/or prevented.

17. A spinal implant as recited in claim 1, wherein the first member comprises an inner surface that faces an inner surface of the second member and an opposite outer surface, the opening extending through the inner surface of the first member and the outer surface, the head comprising a flange that engages the inner surface of the first member.

18. A spinal implant as recited in claim 1, wherein the post comprises an outer surface that includes a thread and the deformable element includes a resiliently biased wall including teeth engageable with the thread, the thread and the teeth each having an angled orientation.

19. A spinal implant as recited in claim 1, wherein the post comprises an outer surface that includes a thread and the deformable element includes a resiliently biased wall including teeth engageable with the thread, the thread extending at an acute angle relative to the outer surface and the teeth each extending an acute angle relative to the resiliently biased wall.

20. A spinal implant comprising:
a first member;
a fastener connected with the first member;
a second member including a deformable element engageable with the fastener such that the second member is translatable relative to the fastener in a first axial direction and translation of the second member relative to the fastener in a second axial direction is resisted and/or prevented; and
a ring comprising an outer surface that engages an inner surface of the deformable element to resist and/or prevent translation in the second direction.

* * * * *